United States Patent
Takemoto et al.

(10) Patent No.: US 7,798,978 B2
(45) Date of Patent: Sep. 21, 2010

(54) BODY FLUID COLLECTING DEVICE

(75) Inventors: Masafumi Takemoto, Nakakoma-gun (JP); Masao Takinami, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 10/592,668

(22) PCT Filed: Mar. 11, 2005

(86) PCT No.: PCT/JP2005/004341
§ 371 (c)(1), (2), (4) Date: Sep. 13, 2006

(87) PCT Pub. No.: WO2005/087103
PCT Pub. Date: Sep. 22, 2005

(65) Prior Publication Data
US 2007/0197936 A1   Aug. 23, 2007

(30) Foreign Application Priority Data
Mar. 15, 2004  (JP) .............................. 2004-073594

(51) Int. Cl.
A61B 5/00   (2006.01)
A61B 17/14  (2006.01)
A61B 17/32  (2006.01)

(52) U.S. Cl. .................. 600/583; 606/181; 606/182
(58) Field of Classification Search ............... 600/183, 600/184, 583; 606/181, 182
See application file for complete search history.

(56) References Cited

U.S. PATENT DOCUMENTS

| 6,071,250 A * | 6/2000 | Douglas et al. ............. 600/583 |
| 6,086,545 A * | 7/2000 | Roe et al. .................. 600/570 |
| 6,261,245 B1 * | 7/2001 | Kawai et al. ............... 600/576 |
| 6,706,159 B2 * | 3/2004 | Moerman et al. ...... 204/403.03 |
| 2003/0109808 A1 * | 6/2003 | Takinami et al. ........... 600/584 |
| 2004/0210247 A1 | 10/2004 | Sonoda et al. |
| 2004/0236251 A1 * | 11/2004 | Roe et al. .................. 600/583 |
| 2005/0085839 A1 * | 4/2005 | Allen et al. ................ 606/181 |

FOREIGN PATENT DOCUMENTS

| JP | 2001-309905 | 11/2001 |
| JP | 2002-34956 | 2/2002 |
| JP | 2002-085384 | 3/2002 |
| JP | 2002-219114 | 8/2002 |

\* cited by examiner

*Primary Examiner*—Max Hindenburg
*Assistant Examiner*—Sean P Dougherty
(74) *Attorney, Agent, or Firm*—Buchanan Ingersoll & Rooney PC

(57) ABSTRACT

A body fluid collecting device is used by mounting a tip with a puncture needle and a front end opening at the front end portion thereof for allowing the puncture needle to pass therethrough. The device additionally includes a device body, having a contact part for fitting skin thereto, a tip mounting part having a storage space formed therein capable of storing the tip, a pump for depressurizing the inside of the storage space, and a movable means. The movable means is capable of moving the front end portion of the tip mounting part along a longitudinal direction of the puncture needle, and within a specified range, when the storage space is depressurized by the pump under a condition in which the tip is stored in the storage space, the skin is fitted to the contact part, and the front end opening is sealed.

3 Claims, 2 Drawing Sheets

BODY FLUID COLLECTING DEVICE

TECHNICAL FIELD

The present invention relates to a body fluid collecting device which is used by mounting a tip provided with a puncture needle with a sharp needle tip at a front end portion thereof.

BACKGROUND ART

In recent years, due to an increase in the number of diabetics, self-measurement of blood sugar by patients themselves, in order to monitor daily variations in blood sugar levels, has been recommended.

For measurement of blood sugar, a blood sugar measuring device is used, which automatically measures blood glucose levels in blood. Prior to such measurement, patients must collect their own blood.

As a method of collecting blood, the skin at a fingertip or the like is punctured with a puncture needle, and then the periphery of the punctured portion is depressed in order to squeeze out blood therefrom.

For carrying out such a method, for example, a component measuring device equipped with a puncture means (tip) having a puncture needle therein may be used, as described in Japanese Patent Laid-open Publication No. 2001-309905. This device operates as follows. First, the tip is mounted on a tip mounting part of the component measuring device, and the skin is fitted against a ring-shaped end portion of the tip. Next, the puncture means provided in the component measuring device is operated in order to cause the puncture needle to project therefrom, thereby puncturing the fingertip. Subsequently, the space, in which the tip is mounted, of the tip mounting part is depressurized, so that blood is sucked out of the punctured portion by depressurization. Further, simultaneously with depressurization, the tip mounting part is moved away from the skin, so as to cancel congestion (blood stasis) of the skin, thereby increasing the amount of bleeding.

In such a component measuring device, however, depending on the punctured portion (the portion punctured by the puncture needle), depressurization of the space may be accompanied by movement of the tip mounting part away from the periphery of the punctured portion, with the result that the tip mounting portion slips away from the periphery of the punctured portion. As a result of such slippage, suction of blood out of the punctured portion stops, so that it becomes difficult to collect blood sufficiently (assuredly). In addition, due to an abrupt canceling of the depressurized condition, blood may be scattered, staining surrounding devices or the like.

DISCLOSURE OF THE INVENTION

It is an object of the present invention to provide a body fluid collecting device, which is capable of preventing a front end side portion of a tip mounting part from being moved excessively in the base end direction and causing the tip to part from the skin.

In order to attain the above object, according to the present invention, there is provided a body fluid collecting device that makes it possible to prevent the front end side portion of the tip mounting part from moving excessively in the base end direction and causing the tip to part from the skin.

The body fluid collecting device according to the present invention makes it possible to assuredly prevent the front end side portion of the tip mounting part from moving excessively in the base end direction and causing the tip to part from the skin.

The body fluid collecting device according to the present invention ensures that air-tightness of the space in the tip mounting part that the tip is maintained securely.

The body fluid collecting device according to the present invention makes it possible to assuredly prevent the front end side portion of the tip mounting part from moving excessively in the base end direction and causing the tip to part from the skin.

The body fluid collecting device according to the present invention ensures that the second portion can move smoothly relative to the device body along the longitudinal direction of the puncture needle.

The body fluid collecting device according to the present invention ensures that the first portion and the second portion can be located respectively at predetermined positions, in a condition prior to performing puncturing by the puncture needle.

The body fluid collecting device according to the present invention ensures that air-tightness of the space in the tip mounting part that stores the tip is maintained assuredly.

The body fluid collecting device according to the present invention makes it possible to puncture the skin assuredly, thereby causing a body fluid to flow out from the punctured portion.

The body fluid collecting device according to the present invention permits the person on whom the test is performed to correctly perceive the amount of the predetermined component in the body fluid.

BEST MODE FOR CARRYING OUT THE INVENTION

The body fluid collecting device according to the present invention shall be described in detail below, based on a preferred embodiment thereof shown in the accompanying drawings. Incidentally, in this embodiment, a case in which the body fluid collecting device of the present invention is applied to a component measuring device shall be described.

Figure 1:
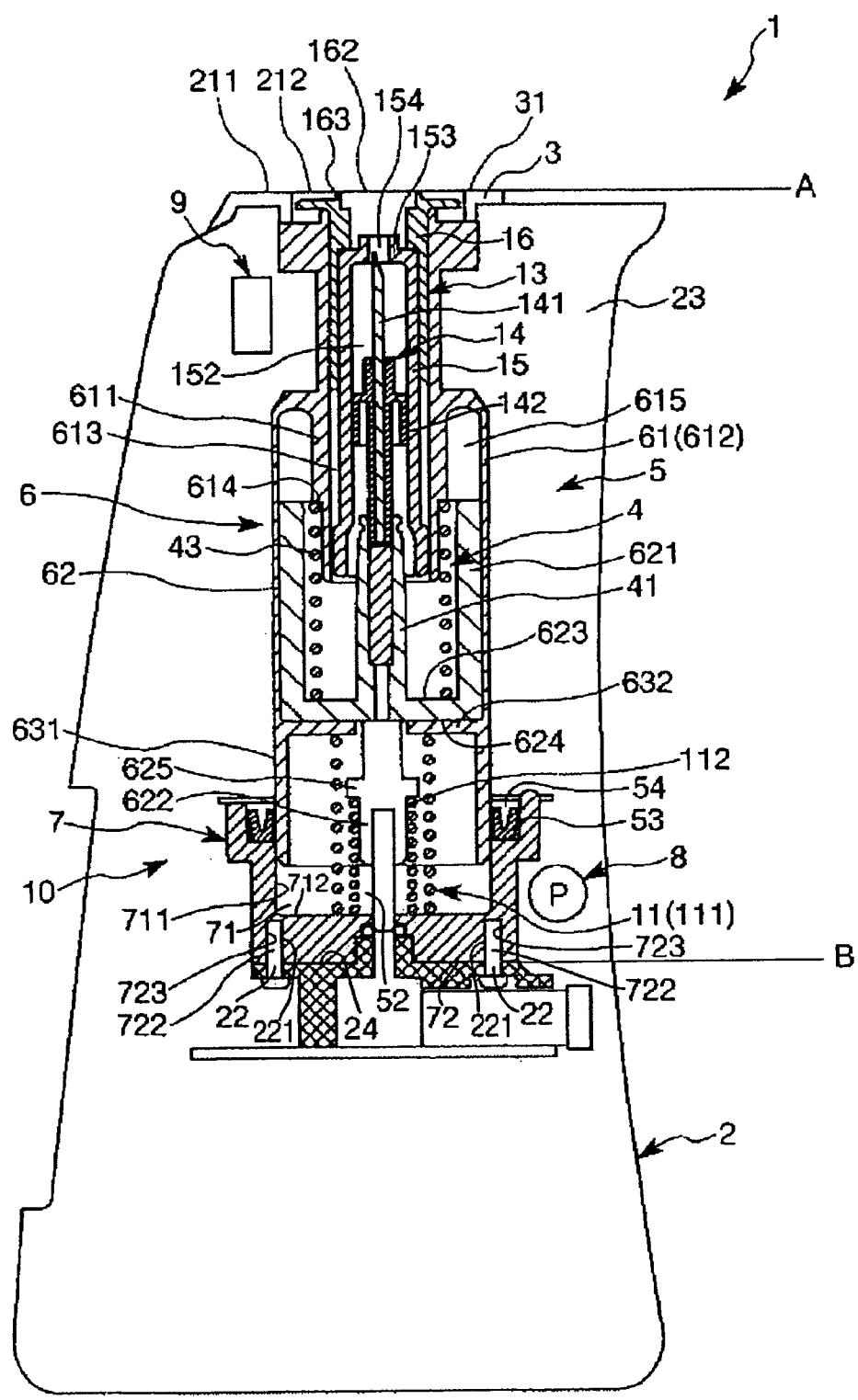
FIG. 1 is a vertical sectional view showing a case in which the body fluid collecting device according to the present invention is applied to a component measuring device.
Figure 2:
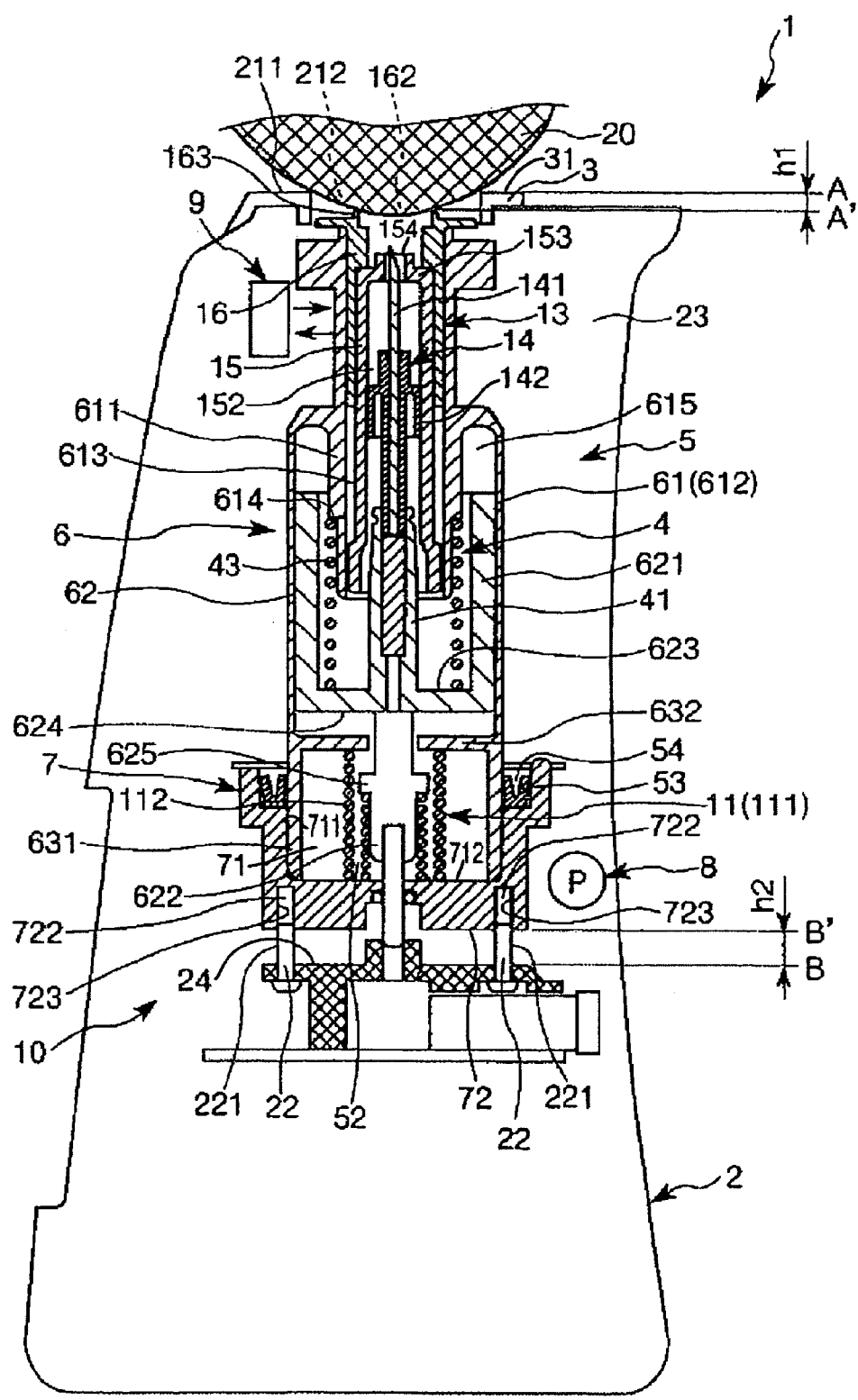
FIG. 2 is a vertical sectional view showing a condition in which a person's skin is fitted onto the component measuring device shown in FIG. 1.

FIG. 1 is a vertical sectional view showing a case in which the body fluid collecting device according to the present invention is applied to a component measuring device, and FIG. 2 is a vertical sectional view showing a condition in which a person's skin is fitted onto (placed in close contact with) the component measuring device shown in FIG. 1. Incidentally, descriptions shall be made while referring to the upper side in FIGS. 1 and 2 as "the front end (side)", and the lower side in FIGS. 1 and 2 as "the base end (side)".

As shown in FIG. 1, the component measuring device (blood component measuring device) 1 is used in a state of being fitted with a tip 13 having a puncture needle 14 having a sharp needle tip and a front end opening 162 (opening) at a front end portion thereof, for permitting the needle tip to pass therethrough. The component measuring device 1 further includes a device body 2, a tip mounting part 5 in which the tip 13 can be removably mounted, a puncture means 4 stored in the tip mounting part 5, a measuring means 9 for measuring a predetermined component in a body fluid (blood), a pump (depressurizing means) 8 for depressurizing the inside of the tip mounting part 5, a control means, and a movable means 10. These component elements shall be described below.

The device body 2 is provided therein with a space 23, in which the above-mentioned component elements and the like are stored.

A front end surface 211 of the device body 2 is formed with an opening 212 that penetrates through the device body 2, providing communication between the inside and the outside. The tip 13 is mounted (held) in the tip mounting part 5 through the opening 212.

In addition, the front end surface 211 is provided with a contact part 3, which surrounds the periphery of the opening 212 and against which the skin is to be pressed. The contact part 3 has a shape corresponding to the shape of the skin pressed against the contact part 3. The contact part 3 includes a contact surface 31 on the front end side thereof. The component measuring device 1 is operated when the skin is placed in contact with the contact part 3 (contact surface 31). By this operation, the skin (hereinafter, in this embodiment, assumed to be a fingertip 20 as a representative example) is punctured, and an amount of a predetermined component in the collected blood (hereinafter, in this embodiment, assumed to be glucose as a representative example) is measured.

In addition, the control means (not shown), which is composed of a microcomputer, is mounted inside the space 23 in the device body 2. The control means controls various operations of the component measuring device 1. Further, the control means incorporates an arithmetic unit therein for calculating the amount of glucose (blood sugar level) in the blood based on a signal from the measuring means 9.

As shown in FIG. 1, the pump (electrically operated pump) 8, which serves as a depressurizing means (suction means), is disposed in the vicinity of the tip mounting part 5. The pump 8, operated by electric power, is connected through a tube (not shown) to a tip storage space 52 (space), which is formed inside of the tip mounting part 5 (described later) and in which the tip 13 can be stored.

The pump 8 sucks and discharges air in the storage space 52 in the tip mounting part 5, thereby depressurizing the storage space 52 in the tip mounting part 5.

In addition, the pump 8 may be of any type that can place the storage space 52 (along with the punctured portion of the fingertip 20) in the tip mounting part 5 in a depressurized state (suction state), and more specifically, at a pressure (for example, about −600 to −300 mmHg) so that blood can be sucked out of the punctured portion of the fingertip 20.

As shown in FIG. 1, the measuring means 9 is disposed in the space 23 inside the device body 2. The measuring means 9 optically measures the amount of glucose in the blood, which is developed on a test paper (not shown) provided in the tip 13. The installation position of the measuring means 9 is set in the vicinity of a side position where the test paper is located, in a condition where the tip 13 is mounted and held in the tip mounting part 5.

The measuring means 9 includes a light emitting element (light emitting diode) and a light receiving element (photodiode), which are not shown in the figure.

The light emitting element is electrically connected to the control means, and the light receiving element is electrically connected to the control means through an amplifier and an A/D converter, which are not shown in the figure.

The light emitting element is operated by a signal from the control means to emit light. Such light is preferably pulsed light, which is emitted intermittently at a predetermined time interval.

When the light emitting element is turned ON, under a condition in which the tip 13 is mounted in the tip mounting part 5, light emitted from the light emitting element is radiated onto the test paper, and reflected light is received by the light receiving element (see FIG. 2) and is subjected to photoelectric conversion. An analog signal in accordance with the quantity of light received is output from the light receiving element, the analog signal is amplified in a desired manner, the amplified signal is then converted by the A/D converter into a digital signal, and the digital signal is input to the control means.

In the control means, a predetermined arithmetic process is conducted, based on the input signal, and correcting calculations are conducted, as required, in order to determine the amount of glucose (blood sugar level) in the blood. The determined blood sugar level is displayed on a display unit (not shown).

Via the measuring means 9, the person undergoing testing (patient) can correctly perceive the amount of glucose in his or her blood.

As described above, the component measuring device 1 is used with the tip 13 mounted in the tip mounting part 5 thereof. As shown in FIG. 1, the tip 13 includes the puncture needle 14, a first housing 15 which slidably houses the puncture needle 14 therein, and a second housing 16 disposed on an outer peripheral portion of the first housing 15.

The puncture needle 14 is composed of a needle body 141 and a hub 142 attached (fixed) to the base end side of the needle body 141, wherein the puncture needle 14 is stored in a cavity part 152 of the first housing 15.

The needle body 141 is composed of either a hollow member or a solid member formed of a metallic material, for example, stainless steel, aluminum, aluminum alloy, titanium, titanium alloy or the like, wherein a front end of the needle body 141 has a sharp cutting edge (needle tip). A surface (skin) of the fingertip 20 is punctured by the cutting edge. In addition, the hub 142 is fitted into a plunger 41, which constitutes part of the puncture means 4 (described later), at a base end portion thereof. The needle body 141 may be a plastic needle, and further, the needle body 141 and the hub 142 may be formed integrally in one piece.

The first housing 15 is composed of a bottomed cylindrical member having a wall part 153 at the bottom thereof, and further includes a cavity part 152 therein. The wall part 153 includes a hole 154 in a roughly central portion thereof. The hole 154 permits the needle body 141 to pass therethrough at the time of puncturing the fingertip (finger) 20.

The second housing 16 is attached to the outer peripheral portion of the first housing 15. The second housing 16 is composed of a roughly cylindrical member, which is provided at its front end with a contact part 163 projecting in a ring shape. The contact part 163 provides a portion against which the fingertip 20 is pressed. The contact part 163 includes a front end opening (opening) 162 on the front end surface thereof, which communicates with the inside of the cavity part 152 of the first housing 15 (and further, with the storage space 52 in the tip mounting part 5), and which permits the needle body 141 (needle tip) to pass therethrough.

As has been mentioned above, the component measuring device 1 includes the movable means 10. The movable means 10 shall now be described in detail below.

As shown in FIG. 1, the tip mounting part 5 has a first portion 6 (first tip mounting part), a second portion 7 (second tip mounting part) provided on the base end side of the first portion 6 so as to be movable relative to the device body 2, and a biasing means 11 for biasing the first portion 6 and the second portion 7 to be spaced away from each other.

The first portion 6 has an outer cylinder part 61, an inner cylinder part 62 disposed inside of the outer cylinder part 61, and a top 622 disposed in abutment with the base end side of the inner cylinder part 62.

The outer cylinder part 61 shown in FIG. 1 has a cylindrical inside portion 611, and a bottomed cylindrical outside portion 612 concentrically disposed around the outer periphery of the base end side of the inside portion 611. The inside portion 611 includes a cavity part 613 along the longitudinal direction thereof, wherein the tip 13 is stored (mounted) in the cavity part 613. The inside portion 611 is provided at its outer periphery on the base end side thereof with a stepped portion 614 reduced in outside diameter. The front end of a coil spring 43 of the puncture means 4 (described later) is disposed in abutment with the stepped portion 614.

The inner cylinder part 62 shown in FIG. 1 has a bottomed cylindrical tube portion 621, and a plunger 41 that extends from a bottom portion of the tube portion 621 toward the front end thereof. The tube portion 621 is inserted into a cavity part 615 of the outside portion 612 of the outer cylinder part 61, wherein its bottom surface 623 on the front end side abuts with the base end of the coil spring 43. The top 622 is roughly columnar in shape, and includes a radially enlarged portion (flange portion) 625 enlarged in diameter.

The outer cylinder part 61 shown in FIG. 1 is roughly tubular in shape, and supports the inner cylinder part 62 therein. In addition, the outer cylinder part 61 has a radially reduced portion 632, which is reduced in diameter.

The second portion 7 is in the shape of a bottomed cylinder, wherein the inner peripheral surface 711 of the cavity part 71 of the second portion 7 and the outer peripheral surface 631 of the outer cylinder part 61 of the first portion 6 slide relative to each other when the first portion 6 and the second portion 7 are moved relative to each other along the longitudinal direction (up-down direction in FIG. 1) of the puncture needle 14 (see FIGS. 1 and 2).

In addition, as shown in FIG. 1, the cavity part 71 communicates with the front end opening 162 of the tip 13 through the cavity parts 615, 613 of the first portion 6, such that the spaces thus communicated constitute the storage space 52 in the tip mounting part 5.

Further, as shown in FIG. 1, the second portion 7 includes a plurality of guide holes 722 on the bottom surface 72 on the base end side. A plurality of guide pins 22 provided on the device body 2 are inserted respectively into the guide holes 722. When the second portion 7 moves relative to the device body 2, the inner peripheral surfaces 723 of the guide holes 722 slide along the outer peripheral surfaces 221 of the guide pins 22 (see FIGS. 1 and 2).

As a result of the guide pins 22 and guide holes 722 described above, the second portion 7 can be moved smoothly relative to the device body 2 along the longitudinal direction of the puncture needle 14.

The biasing means 11 is composed of coil springs 111 and 112, which are disposed within the storage space 52. The front end and the base end of the coil spring 111 abut respectively against the radially reduced portion 632 of the outer cylinder part 61 and the bottom surface 712 of the cavity part 71 of the second portion 7. In addition, the front end and the base end of the coil spring 112 abut respectively against the radially enlarged portion 625 of the top 622 and the bottom surface 712 of the cavity part 71 of the second portion 7.

Due to the biasing means 11 (coil spring 111) thus provided, in a condition before puncturing is performed (hereinafter referred to as "the initial condition"), the first portion 6 and the second portion 7 can be located respectively at predetermined positions in the initial condition. Specifically, as shown in FIG. 1, under the biasing forces of the biasing means 11, the front end of the outer cylinder part 61 abuts with the contact part 3, and the first portion 6 can be located in the space 23 within the device body 2 (as indicated by A in FIG. 1), so that the position (height) of the front end opening 162 of the tip 13 is substantially equal to the position (height) of the front end surface 211 of the device body 2. On the other hand, the second portion 7 can be located (as indicated by B in FIG. 1) such that its bottom surface 72 abuts against the surface 24 of the device body 2 at a position where the guide pins 22 project therefrom.

Incidentally, the material constituting the coil spring 111 is not particularly limited. For example, various metallic materials, or various plastics and the like can be used, either singly or in combination.

The above-described tip mounting part 5 is configured such that the volume of the storage space 52 varies as a result of relative movements between the first portion 6 and the second portion 7. Specifically, since the second portion 7 is not fixed in position, the tip mounting part 5 is configured such that the first portion 6 (the portion on the front end side of the tip mounting part) can be prevented from being forcibly moved in the base end direction, whereas the tip mounting part 5 can be freely moved in the longitudinal direction of the puncture needle 14 by a predetermined distance (contraction distance) generated by contraction of the storage space 52 due to depressurization thereof by the pump 8.

In addition, the tip mounting part 5 is provided with a ring-shaped seal member 53, which maintains air-tightness of the storage space 52 when the first portion 6 and the second portion 7 are moved. The seal member 53 is disposed within a gap 54 between the outer peripheral surface 631 of the outer cylinder part 61 of the first portion 6 and the inner peripheral surface 711 of the cavity part 71 of the second portion 7. The seal member 53 is also in abutment with both the outer peripheral surface 631 and the inner peripheral surface 711.

Due to the seal member 53 described above, air-tightness of the storage space 52 is maintained more securely.

Incidentally, the seal member 53 preferably is formed of an elastic material.

The puncture means 4 shall be described below.

As shown in FIG. 1, the puncture means 4 includes a plunger 41, and a coil spring (biasing member) 43 for biasing the plunger 41 in the base end direction. The puncture means 4 drives the puncture needle 14 in order to puncture the fingertip 20, under a condition in which the tip 13 is stored within the storage space 52, the fingertip 20 is fitted to (placed in close contact with) the contact part 3, and the front end opening 162 is sealed.

The plunger 41 is cup-shaped, and is disposed at the bottom surface 623 of the tube portion 621. The hub 142 of the puncture needle 14 is detachably fitted to the plunger 41.

The coil spring 43 is provided in the first portion 6, so that the front end and base end thereof abut respectively on the stepped portion 614 and on the bottom surface 623 of the first portion 6.

In addition, the coil spring 112 functions as part of the puncture means 4. Specifically, the coil spring 112 extends so as to move the plunger 41 (the inner cylinder part 62) in the front end direction, thereby causing the cutting edge of the needle body 141 to puncture the fingertip 20.

On the other hand, in this instance, the coil spring 43 is contracted, and thus biases the plunger 41 in the base end direction, i.e., tends to push the plunger 41 back toward the base end side. Thereafter, the plunger 41 performs an attenuating motion, coming to rest at a position where the elastic force of the coil spring 112 and the elastic force of the coil spring 43 balance each other (see FIG. 2).

With the puncture means 4 configured as described above, it is possible to puncture the fingertip 20, thereby causing blood to flow out from the punctured portion.

Now, description will be made below concerning a case in which puncturing and blood collection are performed by use of the component measuring device 1.

[1] First, the tip 13 is inserted (stored) in the storage space 52 of the tip mounting part 5 through the opening 212 of the device body 2, and the hub 142 of the puncture needle 14 is fitted (mounted) into the plunger 41 (see FIG. 1).

[2] Next, a fingertip 20 is placed in close contact with the contact part 3. This results in the front end opening 162 of the tip 13 becoming sealed (see FIG. 2). In addition, when the fingertip 20 is pressed against the front end opening 162, the position of the front end opening 162 is moved in the base end direction, i.e., the front end opening 162 is moved from the position A to the position A', as shown in FIG. 2.

[3] Subsequently, as discussed above, the puncture means 4 is operated under control of the control means, in order to cause the needle body 141 of the puncture needle 14 to puncture the fingertip 20. After puncturing has been completed, the needle body 141 is stored in the tip 13.

[4] While in the above-described condition [3], the pump 8 is operated under control of the control means, in order to depressurize the storage space 52. As a result of such depressurization, blood is sucked out of the punctured portion (puncture wound) of the fingertip 20.

In addition, by such depressurization, a force for moving the first portion 6 in the base end direction (hereinafter referred to as "the first force") is exerted on the first portion 6. At the same time, however, since the first portion 6 and the second portion 7 can be moved relative to each other, a force for moving the second portion 7 in the front end direction (hereinafter referred to as "the second force"), against biasing forces of the coil springs 111, 112 and 43, is exerted on the second portion 7. The first force and the second force are equivalent to and balance each other, so that the forces do not act to release (separate) the tip 13 from the fingertip 20. Therefore, the suction condition of the fingertip 20 (the depressurized condition of the storage space 52) is maintained.

[5] Since the skin abuts against the contact surface 31 of the contact part 3, the skin is restricted from moving in the base end direction. In this case, since the tip mounting part 5 is movable, the weight of the tip mounting part 5 acts on the fingertip 20, thereby sealing the front end opening 162 of the tip 13. Since the skin of the finger is pulled in the base end direction, a congestion condition generated by pressing the fingertip 20 against the front end opening 162 is canceled. This permits blood to be sufficiently collected from the punctured portion of the fingertip 20.

In addition, the above configuration ensures that the distance between A and A' shown in FIG. 2 can be made constant, so that the suction force at the fingertip 20 similarly can be made constant. Therefore, the person (patient) performing blood testing can reliably perform the blood component measurement, without requiring first becoming accustomed to, or getting the knack of, use of the component measuring device 1.

Further, the amount of movement of the first portion 6 and the second portion 7 (i.e., the sum of the distances denoted by h1 and h2 in FIG. 2) is usually and preferably 0.5 to 5 mm, and more preferably 1.5 to 3 mm, taking into consideration elasticity of the skin.

In addition, the weight of the tip mounting part 5 (inclusive of the tip 13) is suitably set, so that the tip mounting part 5 will not part from the skin when the skin is pulled for canceling congestion thereof. This weight is usually and preferably 5 to 200 gf, and more preferably 10 to 100 gf.

Further, the configuration of the tip mounting part 5 is not limited to a configuration wherein the first portion 6 and the second portion 7 are moved relative to each other, and wherein the volume of the storage space 52 is varied by such movement. For example, a configuration may be adopted in which the tip mounting part 5 can extend and contract along the longitudinal direction of the puncture needle 14, wherein the volume of the storage space 52 is varied by such extension and contraction. Examples of the mechanism (means) for causing extension and contraction include a bellows, or the like. The extension/contraction mechanism is preferably biased in a direction for extending the tip mounting part 5.

Such a configuration can also produce the above-mentioned effects.

In addition, a seal member preferably is provided, for maintaining air-tightness of the storage space 52 when the tip mounting part 5 is extended or contracted.

This configuration produces the same effects as those mentioned in connection with the above-mentioned seal member 53.

While the component measuring device according to the present invention has been described above based on the embodiments shown in the figures, the invention is not limited to such embodiments. For example, the configurations of each part can be replaced by any other configurations that display the same or equivalent functions.

While glucose (blood sugar level) has been described as a representative example of the component to be measured in the above embodiments, the invention is not limited to measuring glucose levels. For example, the component to be measured may be protein, cholesterol, uric acid, creatinine, alcohol, or inorganic ions such as sodium ion, or the like.

In addition, the skin portion is not limited to a fingertip. For example, the portion may be a palm, a dorsal part of a hand, an arm, an abdomen, a thigh, or the like.

Further, the depressurizing means is not limited to an electrically operated pump. For example, the depressurizing means may be a hand-operated pump, a mechanical pump, or the like.

In addition, the guide pins and guide holes are not limited to being provided respectively on the device body and the second portion. For example, the guide holes may be provided on the device body, and the guide pins may be provided on the second portion.

INDUSTRIAL APPLICABILITY

The body fluid collecting device according to the present invention includes a tip with a puncture needle and a front end opening at a front end portion thereof for allowing the puncture needle to pass therethrough, wherein the body fluid collecting device comprises a device body having a contact part for fitting skin thereto, a tip mounting part having a space formed therein capable of storing the tip, a depressurizing means for depressurizing the inside of the space, and a movable means capable of moving the front end portion of the tip mounting part along a longitudinal direction of the puncture needle, and within a specified range, when the space is depressurized by the depressurizing means under a condition in which the tip is stored in the space, the skin is fitted to the contact part, and the front end opening is sealed. Therefore, since the portion on the base end side of the tip mounting part is not fixed in place, when the space inside the tip mounting part is contracted by depressurization, the portion on the front end side of the tip mounting part can be moved along the longitudinal direction of the puncture needle, by a distance corresponding to the amount of contraction thereof, and can follow movement of the skin, whereby the tip is prevented from becoming spaced (or separated) away from the skin. In addition, since separation of the tip from the skin is prevented, the depressurized condition of the space can be maintained, and therefore blood can be sufficiently collected (i.e., sucked out) from the punctured portion of the skin. Accordingly, the body fluid collecting device according to the present invention demonstrates industrial applicability.

The invention claimed is:

1. A body fluid collecting device comprising:
   a device body comprising an interior space and a forward end at which is located a contact part against which skin is to be pressed;
   a tip positioned in the interior space of the device body, the tip comprising a housing and a puncture needle, the puncture needle being positioned in the housing, the housing possessing a front end opening through which the puncture needle of the tip is adapted to pass, the front end opening being located at a front end portion of the housing, the contact part of the device body surrounding the front end opening at the front end portion of the housing, the front end opening of the housing being sealed when the skin is pressed against the contact part;
   a first tip mounting part movably positioned in the interior space of the device body to move in a longitudinal direction, the first tip mounting part comprising a cylindrical portion possessing a forward end at which is provided an opening, the cylindrical portion also possessing a rearward end portion at an end of the cylindrical portion opposite the forward end, the cylindrical portion surrounding a storage space configured to removably receive the housing and the puncture needle, the storage space communicating with the front end opening of the housing;
   a second tip mounting part movably positioned in the interior space of the device body to move in the longitudinal direction, the second tip mounting part comprising a cylindrical portion, the rearward end portion of the cylindrical portion of the first tip mounting part being movably positioned in the cylindrical portion of the second tip mounting part so that the first and second tip mounting parts are relatively movable in the longitudinal direction;
   depressurizing means for depressurizing the storage space surrounded by the cylindrical portion of the first tip mounting part;
   a spring applying a biasing force to both the first tip mounting part and the second tip mounting part to urge the first and second tip mounting parts away from one another in the longitudinal direction when the depressurizing means is not operating; and
   a seal member directly contacting both the first and second tip mounting parts to maintain air-tightness of the storage space,
   the first and second tip mounting parts being movable toward each other along the longitudinal direction against the biasing force of the spring by depressurization of the storage space during operation of the depressurizing means.

2. The body fluid collecting device as set forth in claim 1, wherein the housing of the tip is one housing, the tip comprising another housing positionable inside the one housing, said another housing possessing a cavity part in which the puncture needle is positioned, said another housing possessing a forward end provided with an opening through which the puncture needle is adapted to pass.

3. A body fluid collecting device comprising:
   a device body comprising an interior space and a forward end at which is located a contact part against which skin is to be pressed;
   a tip positioned in the interior space of the device body, the tip comprising a housing and a puncture needle, the puncture needle being positioned in the housing, the housing possessing a front end opening through which the puncture needle of the tip is adapted to pass, the front end opening being located at a front end portion of the housing, the contact part of the device body surrounding the front end opening at the front end portion of the housing, the front end opening of the housing being sealed when the skin is pressed against the contact part;
   a first tip mounting part movably positioned in the interior space of the device body to move in a longitudinal direction, the first tip mounting part comprising a cylindrical portion possessing a forward end at which is provided an opening, the cylindrical portion also possessing a rearward end portion at an end of the cylindrical portion opposite the forward end, the cylindrical portion surrounding a storage space configured to removably receive the housing and the puncture needle, the storage space communicating with the front end opening of the housing;
   a second tip mounting part movably positioned in the interior space of the device body to move in the longitudinal direction, the second tip mounting part comprising a cylindrical portion, the rearward end portion of the cylindrical portion of the first tip mounting part being movably positioned in the cylindrical portion of the second tip mounting part so that the first and second tip mounting parts are relatively movable in the longitudinal direction;
   depressurizing means for depressurizing the storage space surrounded by the cylindrical portion of the first tip mounting part; and
   first spring applying a biasing force to both the first tip mounting part and the second tip mounting part to urge the first and second tip mounting parts away from one another in the longitudinal direction when the depressurizing means is not operating, wherein
   the first and second tip mounting parts are movable toward each other along the longitudinal direction against the biasing force of the first spring by depressurization of the storage space during operation of the depressurizing means, and wherein
   the first tip mounting part comprises an outer cylindrical part and an inner cylindrical part, the inner cylindrical part being movably positioned inside the outer cylindrical part so that the outer cylindrical part and the inner cylindrical part are relatively movable, and the first tip mounting part further comprising a second spring positioned between the outer cylindrical part and the inner cylindrical part, the second spring applying a biasing force to both the outer cylindrical part and the inner cylindrical part.

* * * * *